(12) United States Patent
Smith et al.

(10) Patent No.: US 8,219,178 B2
(45) Date of Patent: Jul. 10, 2012

(54) METHOD AND SYSTEM FOR PERFORMING INVASIVE MEDICAL PROCEDURES USING A SURGICAL ROBOT

(75) Inventors: David W. Smith, Scottsdale, AZ (US); Regina DeSanctis-Smith, Scottsdale, AZ (US); Alan M. Pitt, Scottsdale, AZ (US); Nicholas Theodore, Phoenix, AZ (US); Neil R. Crawford, Tempe, AZ (US)

(73) Assignee: Catholic Healthcare West, Phoenix, AZ (US)

( * ) Notice: Subject to any disclaimer, the term of this patent is extended or adjusted under 35 U.S.C. 154(b) by 714 days.

(21) Appl. No.: 11/845,557

(22) Filed: Aug. 27, 2007
(Under 37 CFR 1.47)

(65) Prior Publication Data
US 2008/0215181 A1 Sep. 4, 2008

Related U.S. Application Data

(63) Continuation of application No. 11/838,027, filed on Aug. 13, 2007, which is a continuation of application No. 11/676,023, filed on Feb. 16, 2007.

(51) Int. Cl.
*A61B 5/05* (2006.01)
(52) U.S. Cl. .......... 600/424; 600/411; 600/427
(58) Field of Classification Search .......... None
See application file for complete search history.

(56) References Cited

U.S. PATENT DOCUMENTS

| 4,799,062 | A * | 1/1989 | Sanderford, Jr. et al. ..... 342/450 |
|---|---|---|---|
| 5,377,678 | A * | 1/1995 | Dumoulin et al. .......... 600/424 |
| 5,445,150 | A * | 8/1995 | Dumoulin et al. .......... 600/424 |
| 5,808,665 | A * | 9/1998 | Green .......... 348/65 |
| 6,246,898 | B1 * | 6/2001 | Vesely et al. .......... 600/424 |
| 6,251,110 | B1 * | 6/2001 | Wampler .......... 606/49 |
| 6,280,383 | B1 | 8/2001 | Damadian |
| 6,400,980 | B1 | 6/2002 | Lemelson |
| 6,675,810 | B2 | 1/2004 | Krag |
| 6,697,664 | B2 * | 2/2004 | Kienzle, III et al. .......... 600/427 |
| 6,701,176 | B1 * | 3/2004 | Halperin et al. .......... 600/411 |
| 6,738,656 | B1 * | 5/2004 | Ferre et al. .......... 600/426 |
| 6,833,814 | B2 * | 12/2004 | Gilboa et al. .......... 342/448 |
| 6,837,892 | B2 | 1/2005 | Shoham |
| 7,015,859 | B2 * | 3/2006 | Anderson .......... 342/450 |
| 7,164,968 | B2 * | 1/2007 | Treat et al. .......... 700/245 |
| 8,010,181 | B2 * | 8/2011 | Smith .......... 600/424 |
| 2003/0060702 | A1 * | 3/2003 | Kuth et al. .......... 600/424 |
| 2004/0097806 | A1 | 5/2004 | Hunter et al. |
| 2004/0171924 | A1 * | 9/2004 | Mire et al. .......... 600/407 |
| 2005/0113659 | A1 * | 5/2005 | Pothier et al. .......... 600/372 |
| 2005/0154376 | A1 * | 7/2005 | Riviere et al. .......... 606/1 |
| 2005/0203382 | A1 * | 9/2005 | Govari et al. .......... 600/424 |
| 2005/0222554 | A1 * | 10/2005 | Wallace et al. .......... 606/1 |
| 2005/0240125 | A1 * | 10/2005 | Makin et al. .......... 601/2 |
| 2006/0111704 | A1 * | 5/2006 | Brenneman et al. .......... 606/41 |
| 2006/0200026 | A1 * | 9/2006 | Wallace et al. .......... 600/424 |
| 2006/0241588 | A1 | 10/2006 | Heim et al. |
| 2007/0021738 | A1 * | 1/2007 | Hasser et al. .......... 606/1 |
| 2007/0113860 | A1 * | 5/2007 | Anderson .......... 128/898 |

(Continued)

*Primary Examiner* — Long V. Le
*Assistant Examiner* — Angela M Hoffa
(74) *Attorney, Agent, or Firm* — Ballard Spahr LLP

(57) ABSTRACT

A method and system for performing invasive procedures includes a surgical robot which is controlled by a guidance system that uses time of flight calculations from RF transmitters embedded in the robot, surgical instrument, and patient anatomy. Sensors around the room detect RF transmissions emitted by the RF transmitters and drive the robot according to a preprogrammed trajectory entered into the guidance system.

19 Claims, 11 Drawing Sheets

U.S. PATENT DOCUMENTS

| | | |
|---|---|---|
| 2007/0129633 A1* | 6/2007 | Lee et al. .................. 600/439 |
| 2007/0135803 A1* | 6/2007 | Belson ........................ 606/1 |
| 2007/0197896 A1* | 8/2007 | Moll et al. ................. 600/407 |
| 2007/0238985 A1* | 10/2007 | Smith et al. ................ 600/424 |
| 2008/0154389 A1* | 6/2008 | Smith et al. ................ 700/24 |
| 2008/0294285 A1 | 11/2008 | Shoham |

* cited by examiner

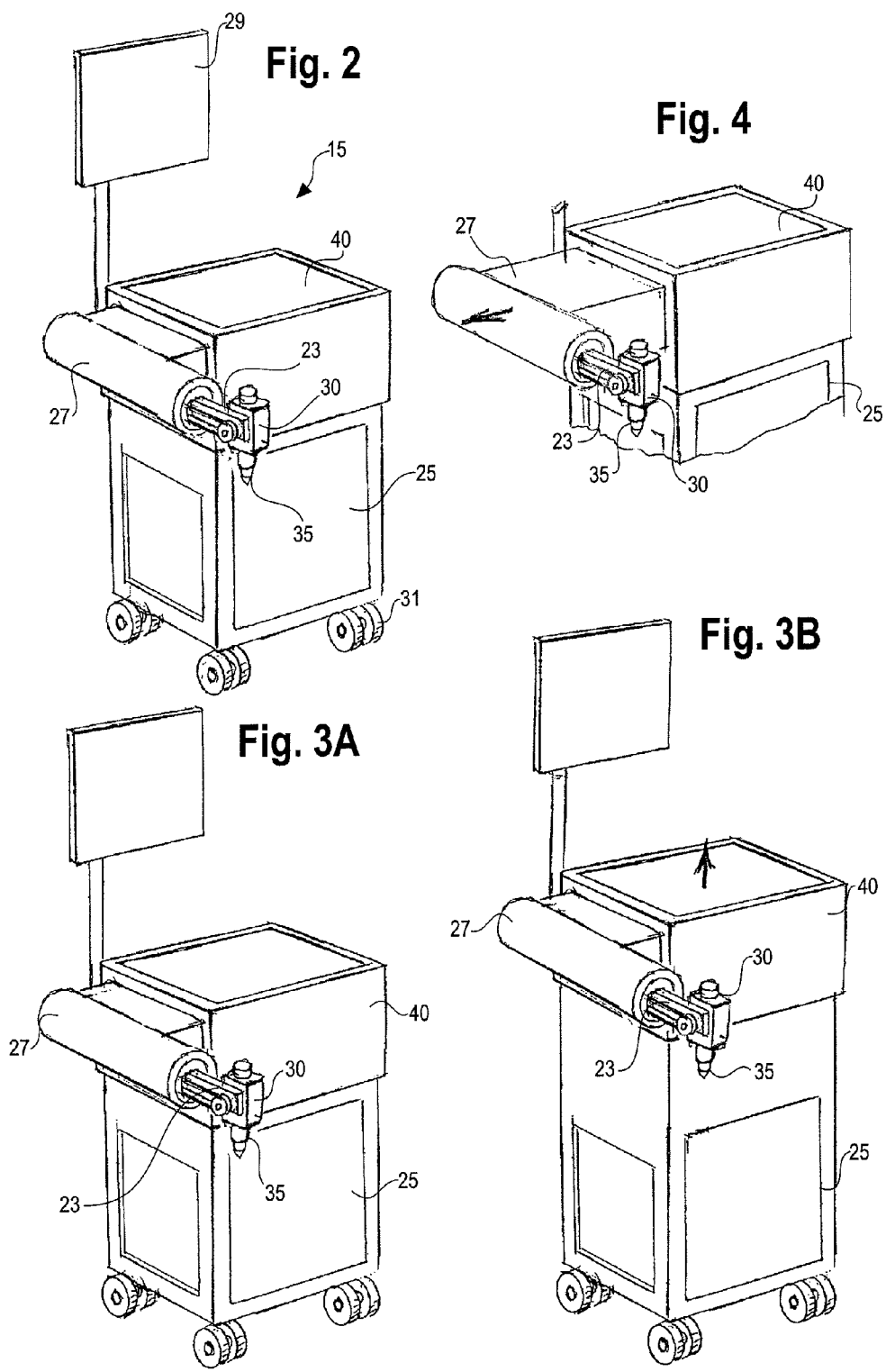

METHOD AND SYSTEM FOR PERFORMING INVASIVE MEDICAL PROCEDURES USING A SURGICAL ROBOT

CROSS-REFERENCE TO RELATED APPLICATIONS

This application is a continuation in part of U.S. patent application Ser. No. 11/838,027, filed Aug. 13, 2007, which is a continuation in part of U.S. Ser. No. 11/676,023, filed Feb. 16, 2007 that is entitled "System Utilizing Radio Frequency Signals For Tracking And Improving Navigation Of Slender Instruments During Insertion Into The Body." This application is related to, but does not claim priority of, U.S. Provisional Patent Application Ser. Nos. 60/775,816 and 60/774,586, both of which were filed on Feb. 16, 2006. The content of all four of the above-referenced applications is incorporated by reference into this application as if fully set forth herein.

FIELD OF THE INVENTION

This invention generally relates to the use of robots in medical procedures and, more particularly, to a method and system of controlling the movement of an end effectuator disposed on a robot arm by means of, for example, time of flight measurements of radio frequency ("RF") signals that are emitted from inside a patient and that are received by at least three RF receivers positioned near where the procedure is taking place.

BACKGROUND OF THE INVENTION

Various medical procedures require the precise localization of a three-dimensional position of a surgical instrument within the body in order to effect optimized treatment. For example, some surgical procedures to fuse vertebrae require that a surgeon drill multiple holes into the bone structure at precise locations. To achieve high levels of mechanical integrity in the fusing system and to balance the forces created in the bone structure it is necessary that the holes are drilled at the correct precise location. Vertebrae, like most bone structures, have complex shapes made up of non-planar curved surfaces making precise and perpendicular drilling difficult. Conventionally, a surgeon manually holds and positions a drill guide tube by using a guidance system to overlay the drill tube's position onto a three dimensional image of the bone structure. This manual process is both tedious and time consuming. The success of the surgery is largely dependent upon the dexterity of the surgeon who performs it.

Limited robotic assistance for surgical procedures is currently available. For example, the da Vinci medical robot system (Intuitive Surgical Inc., Sunnyvale, Calif.) is a robot used in certain surgical applications. In the da Vinci system, the user controls manipulators that control a robotic actuator. The system converts the surgeon's gross movements into micro-movements of the robotic actuator. Although the da Vinci system eliminates hand tremor and provides the user with the ability to work through a small opening, like many of the robots commercially available today, it is expensive, obtrusive, and the setup is cumbersome. Further, for procedures such as thoracolumbar pedicle screw insertion, these conventional methods are known to be error-prone and tedious.

One of the characteristics of the da Vinci system that makes it error prone is that, like many of the current robots used in surgical applications, it uses an articular arm based on a series of rotational joints. The use of an articular system creates difficulties in arriving at a precisely targeted location because the level of any error is increased over each joint in the articular system.

SUMMARY OF INVENTION

In one embodiment, the present invention provides a surgical robot and an imaging system that utilize a Cartesian positioning system as opposed to an articular positioning system. This feature allows, for example, the movement of an effectuator element that forms or is attached to the end of a surgical robot to be individually controlled on the x, y and z axes. This feature also allows the roll, pitch and yaw of the effectuator element to be controlled without creating movement on the x, y or z axes.

The effectuator element can include a guide tube, a tool, or a penetrating shaft with a leading edge that is either beveled (shaft cross-cut at an angle) or non-beveled (shaft ending in a pointed tip). In an exemplary embodiment, a non-beveled effectuator element is employed that is capable of ablating a pathway through tissue to reach the target position and will not be subjected to the lateral mechanical forces and deflection created by a typical beveled tissue penetrating system.

In accordance with an exemplary embodiment, a surgical robot includes three linear motors that separately control movement of the effectuator element on the x, y and z axes. These separate motors allow, for example, a degree of precision to be obtained that is not provided by conventional surgical robots. This aspect of the invention gives the surgeon the capability of exactly determining position and strike angles on a three dimensional image.

Another exemplary aspect of the present invention involves the use of at least one RF transmitter that is mounted on an effectuator element of the surgical robot or on a medical instrument that is held by the effectuator element. Three or more RF receivers are mounted in the vicinity of the surgical robot. The precise location of the RF transmitter and, therefore, the surgical instrument formed or held by the end effectuator can be precisely determined by analyzing the RF signals that are emitted from the RF transmitter. By measuring the time of flight of the RF signal from the transmitter to the RF receivers that are positioned at known locations, the position of the end effectuator element with respect to a patient can be determined. A doctor or surgeon can utilize this aspect of the present invention to, for example, perform epidural injections of steroids into a patient to alleviate back pain without the use of x-rays or fluoroscopy as is currently commonly done.

A still further exemplary aspect of the present invention involves the use of RF feedback to actively control the movement of a surgical robot. To do this control, RF signals are sent by the RF transmitter on an iterative basis and then analyzed in an iterative process to allow, for example, the surgical robot to automatically move the effectuator element to a desired location within a patient's body. The location of the effectuator element and surgical instrument are dynamically updated and can be, for example, displayed to a user in real-time.

The present invention also contemplates a system where RF transmitters are disposed on other elements of the surgical robot, or anywhere within the room where the invasive procedure is taking place, in order to track other devices.

The present invention also contemplates a system where RF transmitters are disposed on the anatomical part of the patient that is the target of the invasive procedure. This system can be used, for example, to correct the movement of the surgical robot in the event the anatomical target moves during the procedure.

In one embodiment, the present invention contemplates a new mechanical system, new component development and improved imaging methods designed with an integrated software architecture that would combine image guidance, medical imaging and a robotic positioning system.

The current invention also contemplates a system that will automatically position and rigidly hold, for example, a guide tube that is precisely aligned with the required trajectory of a pedicle screw during pedicle screw insertion procedures. In case of movement of the patient, the system would automatically adjust the position of the robot to maintain constant alignment relative to the anatomical region of interest.

BRIEF DESCRIPTION OF THE DRAWINGS

The benefits and advantages of the present invention will become more readily apparent to those of ordinary skill in the relevant art after reviewing the following detailed description and accompanying drawings, wherein:

FIG. 2 is a perspective view of a surgical robot according to an embodiment of the present invention;

FIGS. 3A & 3B are perspective views of the surgical robot illustrated in FIG. 2, which show the movement of the base of the surgical robot in the z-axis direction;

FIG. 4 is a partial perspective view of the surgical robot of FIG. 2 which shows how the robot arm can be moved in the x-axis direction;

DETAILED DESCRIPTION OF THE INVENTION

Figure 1:
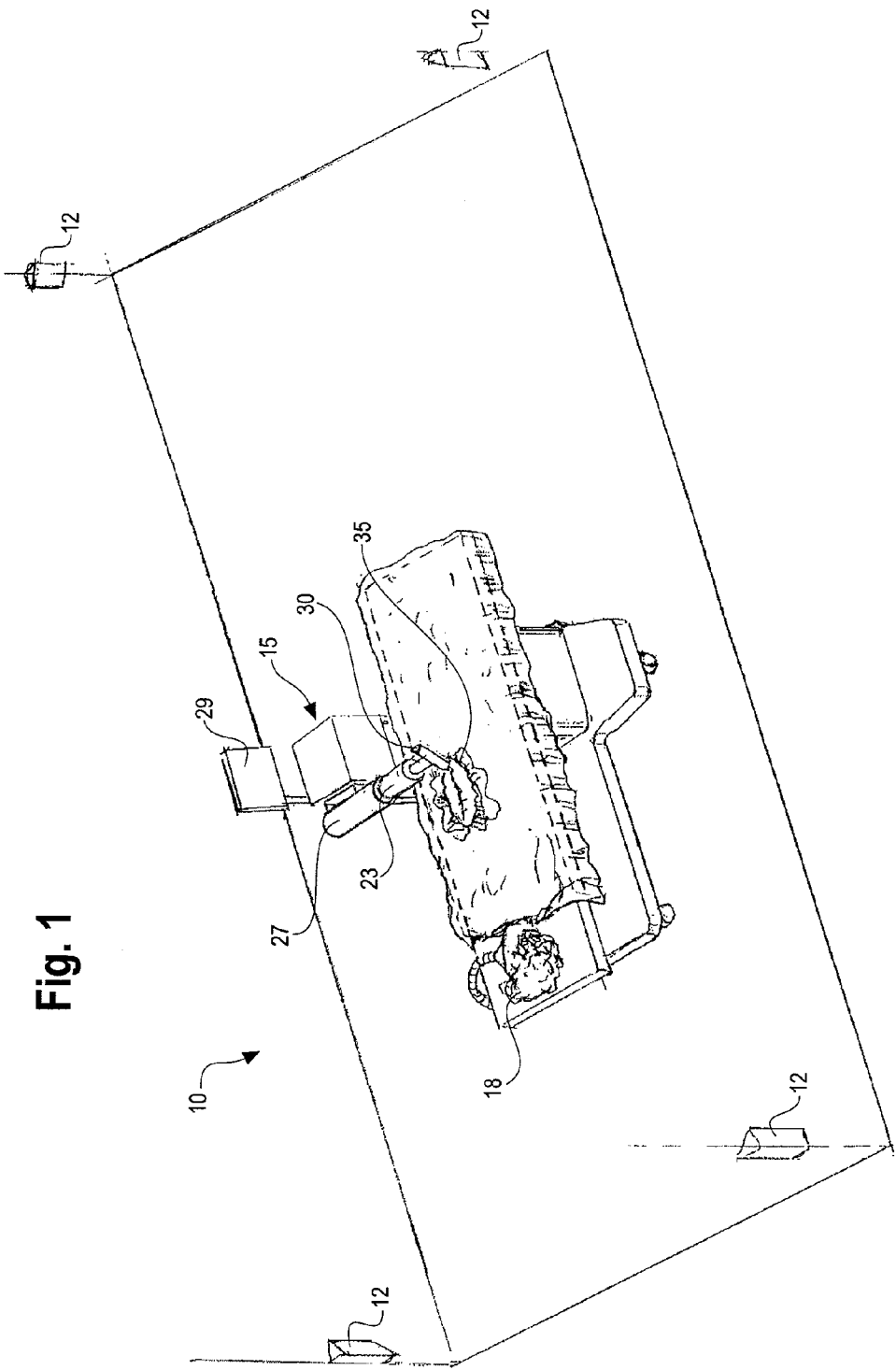
FIG. 1 is a partial perspective view of a room in which an invasive medical procedure is taking place by means of a surgical robot the movement of which is controlled by analysis of RF signals that are emitted from inside the patient and received by RF receivers mounted therein.

While the present invention is susceptible of embodiment in various forms, there is shown in the drawings and will hereinafter be described a presently preferred embodiment with the understanding that the present disclosure is to be considered an exemplification of the invention and is not intended to limit the invention to the specific embodiment illustrated. It should be further understood that the title of this section of this specification, namely, "Detailed Description Of The Invention", relates to a requirement of the United States Patent Office, and does not imply, nor should be inferred to limit the subject matter disclosed herein.

Referring now to FIG. 1, it is seen that in one embodiment of the surgical robot system, a room 10 where an invasive procedure is occurring includes a surgical robot 15, a patient 18 and positioning sensors 12. Surgical robot 15 includes a display means 29, and a housing 27 which contains a robot arm 23. Robot arm 23 is attached to end effectuator 30. In one embodiment, surgical instrument 35 is removably attached to end effectuator 30. In another embodiment, the end effectuator 30 itself forms an instrument that is used to allow an invasive procedure to take place.

In an embodiment of the invention, prior to an invasive procedure, a 3D image scan is taken of the desired surgical area of patient 18 and sent to a computer (not shown) in communication with surgical robot 15. A physician then programs a desired point of insertion and trajectory for surgical instrument 35 to reach the desired anatomical target in patient 18. This desired point of insertion and trajectory is planned on the 3D image scan which is displayed on display means 29. For example, a physician can plan the desired insertion point and trajectory on a computed tomography (CT) scan of patient 18.

One aspect of the present invention involves the use of a local positioning system (LPS) to track the position of surgical instrument 35. A general description of the LPS system follows. An RF transmitter is affixed at a known location on either the end effectuator 30 or the medical instrument 35. Three or more RF receivers are positioned at known locations within, for example, the room where the invasive procedure is to take place. Preferably, the RF receivers are not located in the same plane that is parallel to the floor of the room where the procedure is performed.

To calculate the position of the RF transmitter, the time of flight of the RF signal from the RF transmitter to each one of the RF receivers is measured. Because the velocity of the RF signal is known, the time of flight measurements result in at least three distance measurements, one from each RF receiver.

The memory of a control device that performs the time of flight calculations can include, for example, a geometrical description of the location of the RF transmitter with respect to the operative end of the medical instrument 35 or end effectuator 30 that is utilized to perform or assist in performing an invasive procedure. By doing so, the position of the RF transmitter as well as the dimensional profile of the medical instrument or the effectuator element itself can be displayed on a monitor that is viewed by the person performing the invasive procedure. As one example, the end effectuator element 30 can be a tubular element that is positioned at a desired location with respect to, for example, a patient's spine in connection with the performance of a spinal surgery. The tubular element can be aligned with the z axis defined by corresponding robot motor or, for example, can be disposed at an angle relative thereto. In either case, the control device takes the orientation of the tubular element and the position of the RF transmitter into account.

Another aspect of the present invention involves the utilization of a robot that is capable of moving the end effectuator 30 in x, y and z directions that are orthogonal to each other independently of each other or in any combination. For example, the end effectuator 30 can be moved a given distance along the x axis without causing any movement along the y or z axes. The roll, pitch and yaw and the end effectuator 30 also can be selectively controlled. This aspect of the present invention is advantageous because, for example, its use allows invasive medical procedures to take place with a significantly improved accuracy compared to conventional robots that utilize, for example, a six-degree-of-freedom robot arm. A more complete description of these and other aspects of the invention follows.

Referring to FIG. 1, positioning sensors 12 receive RF signals from RF transmitters (not pictured) located within room 10. These RF transmitters are disposed on various points on surgical robot 10 and/or on patient 18. For example, RF transmitters are attached to housing 27, robot arm 23, end effectuator 30 and surgical instrument 35. Positioning sensors 12, which in an exemplary embodiment comprise RF receivers that are in communication with a computer (not pictured), receive the signal from the RF transmitters. Each transmitter transmits on a different frequency so the identity of each transmitter in the room is determinable. The location of the RF transmitters, and consequently the objects to which the transmitters are attached, are calculated by the computer using time of flight algorithms.

The computer (not pictured) is also in communication with surgical robot 15, and moves surgical robot 15 according to the preplanned trajectory entered prior to the procedure. The position of surgical instrument 35 is dynamically updated so that surgical robot 15 is aware of the location of surgical instrument 35 location at all times during the procedure. Consequently, surgical robot 15 can move surgical instrument 35 to the desired position quickly with minimal damage to patient 18 and without any further assistance from a physician unless the physician so desires. Surgical robot 15 can also correct the path if surgical instrument 35 strays from the desired trajectory.

The physician or other user of the system has the option to stop, modify, or manually control the autonomous movement of surgical robot 15. Further, tolerance controls are preprogrammed into surgical robot 15, which adjust the movement of the surgical robot 15 if certain conditions are met. For example, if the surgical robot 15 cannot detect the positions of surgical instrument 35 because of a malfunction in the RF transmitter attached thereto, it will stop movement. Another example is if surgical robot 15 detects a resistance above a tolerance level, then it will stop movement.

In a preferred embodiment of the invention, display means 29 is a monitor attached to surgical robot 15. Alternatively, display means 29 is not attached to surgical robot 15, but is located either within surgical room 10 or in a remote location.

The computer for use in the system (not pictured), can be located within surgical robot 15, or, alternatively, in another location within surgical room 10 or in a remote location. The computer is in communication with positioning sensors 12 and surgical robot 15.

The surgical robot can also be used with existing guidance systems. Alternative guidance systems are within the scope and spirit of the invention. For instance, an optical tracking system for tracking the location of the surgical device. A commercially available infrared optical tracking system, such as Optotrak (Northern Digital, Waterloo, Ontario, Canada), can be used to track the patient movement and the robot's base location and used with the guidance system. Optical systems require the use of optical markers, which are markers that emit or reflect light, attached to the surgical device. Light emitted from the markers is read by cameras or optical sensors. The location of the object is calculated through triangulation.

Referring now to FIG. 2, it is seen that one embodiment of the surgical robot is shown. The surgical robot includes a base 25 connected to wheels 31. Case 40 is slidably attached to base 25 so that case 40 can slide up and down on a z-axis line perpendicular to the surface on which base 25 sits. Surgical robot also includes a display means 29, and a housing 27 which contains arm 23. Arm 23 is connected to an end effectuator 30. Surgical instrument 35 is removably attached to end effectuator 30.

Surgical instrument 35 can be any instrument used in a medical procedure, both invasive or non-invasive. Surgical instrument 35 may be, for example, a catheter, a probe, a sensor, needle, scalpel, forceps, or any other instrument used in a surgical, non-invasive, or diagnostic procedure. Surgical instrument 35 can also be a biological delivery device apparatus, such as a syringe, which can distribute biologically acting compounds throughout the body. The plunger of the syringe may be manually pressed by a user or automatically compressed by the system once the desired target is reached.

The surgical robot is moveable in a plurality of axes in order to improve the ability to precisely reach a target location. The robot moves on a Cartesian positioning system, that is, movements in different axes can occur relatively independently instead of at the end of a series of joints.

Referring now to FIGS. 3A and 3B, the movement of case 40 relative to base 25 is shown. Case 40 can raise and lower relative to the base 25 in the z-axis direction.

In a preferred embodiment of the invention, housing 27 is attached to case 40 and moves in the z-direction with case 40 when case 40 is raised and lowered. Consequently, arm 23, end effectuator 30 and surgical instrument 35 move with case 40 as case 40 is raised and lowered relative to base 25.

Referring now to FIG. 4, housing 27 is slidably attached to case 40 so that it can extend and retract in a x-axis direction relative to case 40 and perpendicular to the direction case 40 moves relative to base 25. Consequently, arm 23, end effectuator 30 and surgical instrument 35 move with housing 27 as housing 27 is extended and retracted relative to case 40.

Figure 5A:
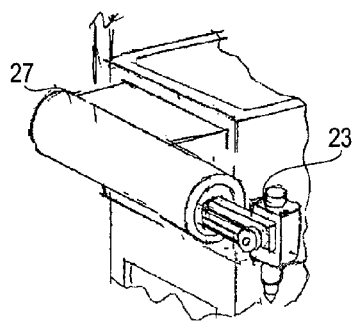
FIGS. 5A & 5B are partial perspective views of the surgical robot of FIG. 2, which show how the robot arm can be moved in the y-axis direction.
Figure 5B:
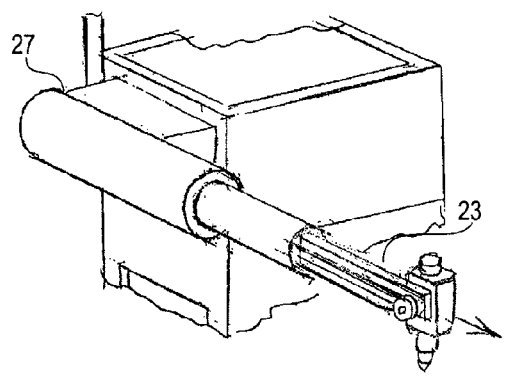

Referring now to FIGS. 5A and 5B, the extension of arm 23 along the y-axis is shown. Arm 23 is extendable on the y-axis relative to case 40, base 25, and housing 27. Consequently, end effectuator 30 and surgical instrument 35 move with arm 23 as arm 23 is extended and retracted relative to housing 27. In an embodiment of the invention, arm 23 is attached to a low profile rail system (not shown) which is encased by housing 27.

Figure 6:
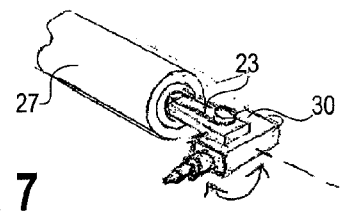
FIG. 6 is a perspective view of a portion of the robot arm of FIG. 2 showing how an effectuator element can be twisted about a y-axis.
Figure 7:
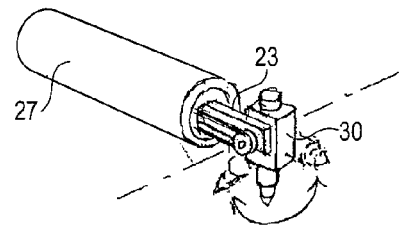
FIG. 7 is a perspective view of a portion of a robot arm of FIG. 2 showing how an effectuator element can be pivoted about a pivot axis that is perpendicular to the y-axis.
Figure 8A:
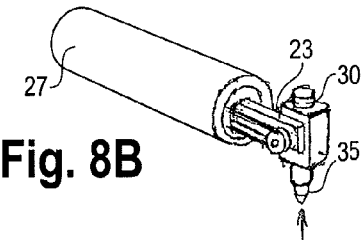
FIGS. 8A & 8B are partial perspective views of the surgical robot of FIG. 2, which show the movement of a surgical instrument along the z-axis from an effectuator element.
Figure 8B:
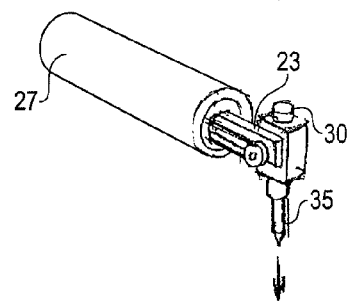

Referring now to FIGS. 6, 7 and 8, the movement of the end effectuator 30 is shown. FIG. 6 shows end effectuator 30 is capable of rotating along the x axis. FIG. 7 shows end effectuator 30 is capable of rotating along the y-axis. FIG. 8 shows end effectuator 30 is capable of raising and lowering surgical instrument 35 on the z axis.

Figure 9:
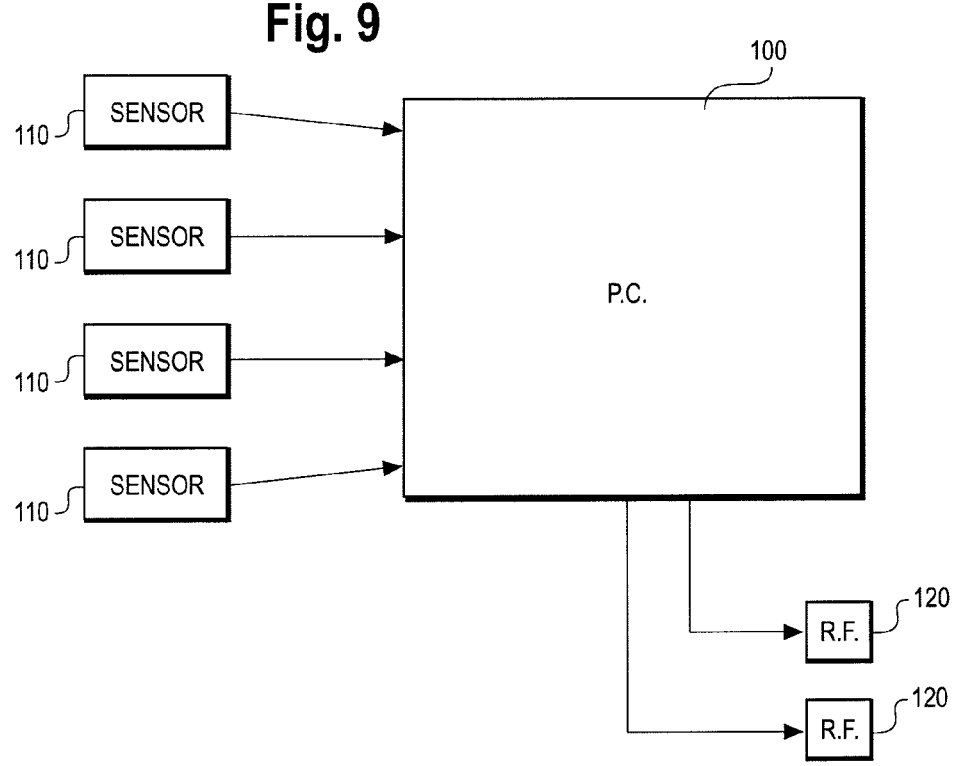
FIG. 9 is a system diagram that shows the local positioning sensors, controlling PC, and Radiofrequency (RF) transmitter.

Referring now to FIG. 9, a system diagram of the positioning sensors 110, computer 100, and RF transmitters 120 is provided. Computer 100 is in communication with positioning sensors 110. In operation, RF transmitters 120 are attached to various points on the surgical robot. RF transmitters 120 may also be attached to various points on or around the anatomical target. Computer 100 sends a signal through a wired connection to RF transmitters 120, prompting RF transmitters 120 to transmit RF signals. The RF signals are read by positioning sensors 110. Positioning sensors 110 are in communication with computer 100, which calculates the location of the positions of all the RF sensors based on time-of-flight information received from the positioning sensors 110. Computer 100 dynamically updates the calculated location of the surgical device being used in the procedure, which is displayed to the user.

Alternatively, computer 100 can be wirelessly connected to RF transmitters 120.

Figure 10:
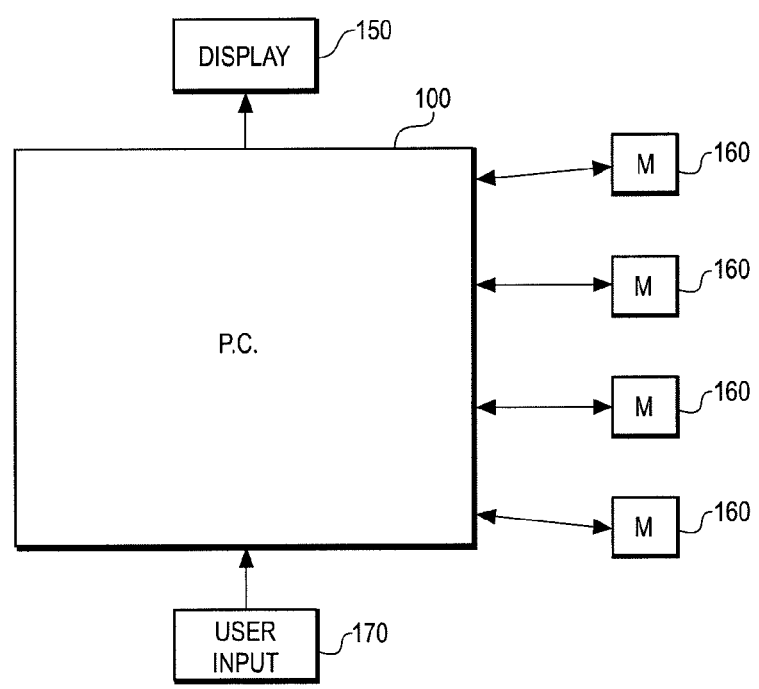
FIG. 10 is a system diagram of the controlling PC, user input, and motors for controlling the robot.

Referring now to FIG. 10, a system diagram of computer 100, display 150, user input 170, and motors 160 is provided. Motors 160 are installed in the surgical robot and control the movement of the surgical robot as described above. Computer 100, which dynamically updates the location of the surgical device being used in the procedure, sends the appropriate signals to the motors 160 so that surgical robot reacts accordingly in response to information received by computer 100. For example, computer 100 prompts motors 160 to move the surgical device along a preplanned trajectory.

The user uses input 170 to plan the trajectory of the desired navigation prior to the invasive procedure. If the user wants to make changes in the invasive procedure after it has commenced, he can use user input 170 to make the desired changes. Computer 100 will then send the appropriate signals to motors 160 in response to the user input.

In a preferred embodiment of the invention, motors 160 are pulse motors providing direct drive, or driving a belt drive and pulley combination attached to the surgical instrument used in the procedure. Alternatively, motors 160 are pulse motors and are attached to a belt drive rack-and-pinion system, or similar power transmission components.

Figure 11:
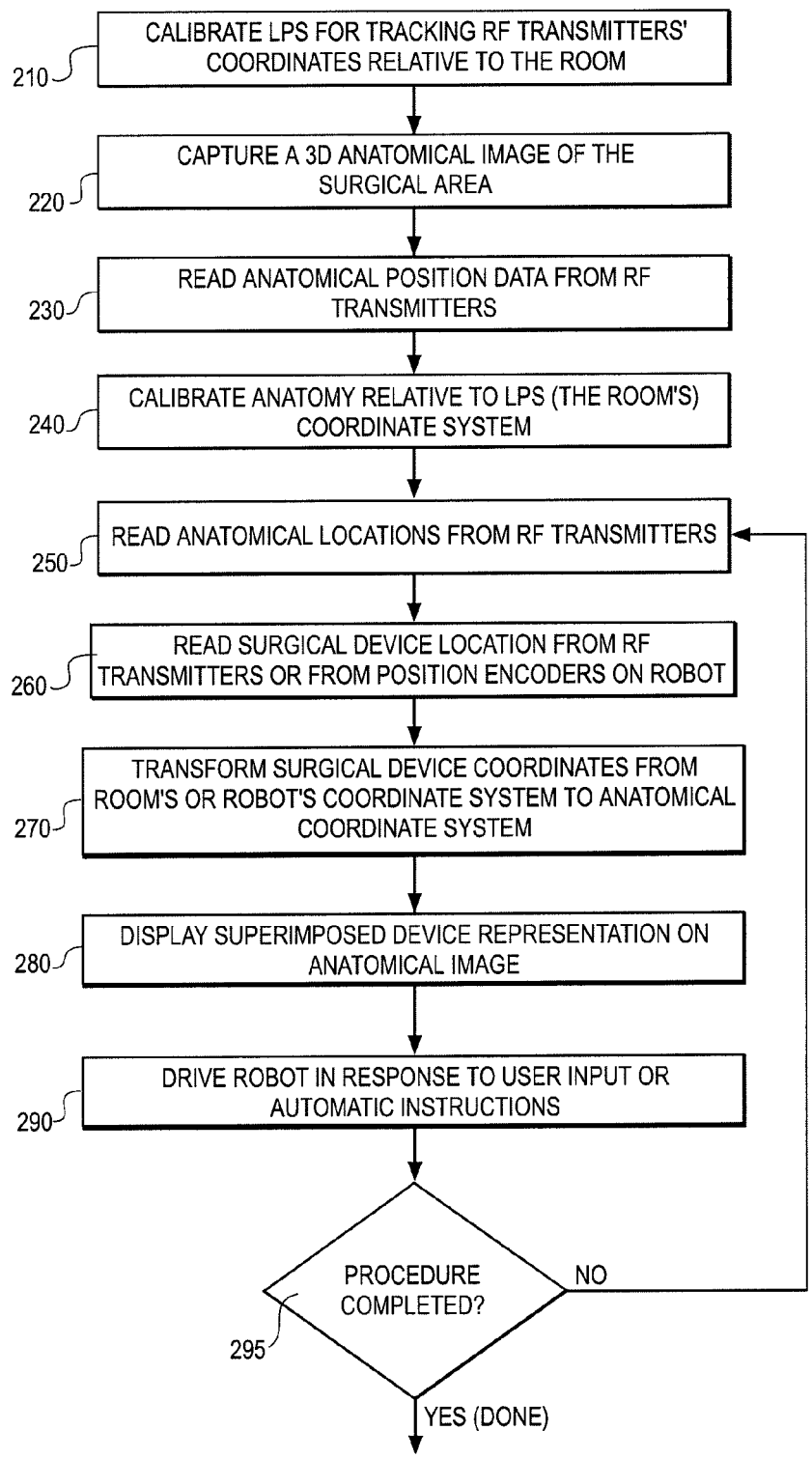
FIG. 11 is a flow chart diagram for general operation of the surgical robot according to an embodiment of the present invention.

Referring now to FIG. 11, a flow chart diagram for general operation of the robot according to an embodiment of the invention is shown.

At step 210, the local positioning system (LPS) establishes a spatial coordinate measuring system for the room where the invasive procedure is to occur; in other words, the LPS is calibrated. In order to calibrate the LPS, a mechanical fixture that includes a plurality of calibrating transmitters attached thereto is placed within the room where positioning sensors are located. At least three calibrating transmitters are required, but any number of calibrating transmitters above three is within the scope of the invention. Also, at least three positioning sensors are required, but any number of positioning sensors above three is also within the scope of the invention, and the accuracy of the system is increased with the addition of more positioning sensors.

The distance between each of the calibrating transmitters relative to each other is measured prior to calibration step 210. Each calibrating transmitter transmits RF signals on a different frequency so the positioning sensors can determine which transmitter emitted a particular RF signal. The signal of each of these transmitters is received by positioning sensors. Since the distance between each of the calibrating transmitters is known, and the sensors can identify the signals from each of the calibrating transmitters based on the known frequency, the positioning sensors are able to calculate, using time of flight calculation, the spatial distance of each of the positioning sensors relative to each other. The system is now calibrated. As a result, the positioning sensors can now determine the spatial position of any new RF transmitter introduced into the room relative to the positioning sensors.

At step 220, a 3D anatomical image scan, such as a CT scan, is taken of the anatomical target. Any 3D anatomical image scan may be used with the surgical robot and is within the scope of the present invention.

At step 230, the positions of the RF transmitters tracking the anatomical target are read by positioning sensors. These transmitters identify the initial position of the anatomical target and any changes in position during the procedure.

If any RF transmitters must transmit through a medium that changes the RF signal characteristics, then the system will compensate for these changes when determining the transmitter's position.

At step 240, the positions of the transmitters on the anatomy are calibrated relative to the LPS coordinate system. In other words, the LPS provides a reference system, and the location of the anatomical target is calculated relative to the LPS coordinates. To calibrate the anatomy relative to the LPS, the positions of transmitters affixed to the anatomical target are recorded at the same time as positions of temporary transmitters on precisely known landmarks on the anatomy that can also be identified on the anatomical image. This calculation is performed by a computer.

At step 250, the positions of the RF transmitters that track the anatomical target are read. Since the locations of the transmitters on the anatomical target have already been calibrated, the system can easily determine if there has been any change in position of the anatomical target.

At step 260, the positions of the transmitters on the surgical instrument are read. The transmitters may be located on the surgical instrument itself, and/or there may be transmitters attached to various points of the surgical robot.

In an embodiment of the invention, the surgical robot also includes a plurality of position encoders attached thereto that help determine the position of the surgical instrument. Position encoders are devices used to generate an electronic signal that indicates a position or movement relative to a reference position. There are many ways to generate a position signal, including for example, magnetic sensors, capacitive sensors, and optical sensors.

Position data read from the position encoders may be used to determine the position of the surgical instrument used in the procedure, and may be redundant of position data calculated from RF transmitters located on the surgical instrument. Therefore, position data from the position encoders may be used to double-check the position being read from the LPS.

At step 270, the coordinates of the positions of the transmitters on the surgical instrument, and/or the positions read from the position encoders, is transformed relative to the anatomical coordinate system. In other words, the position data of the surgical instrument is synchronized into the same coordinate system as the anatomy. This calculation is performed automatically by the computer since the positions of the transmitters on the anatomical target and the positions of the transmitters on the surgical instrument are in the same coordinate system and the positions of the transmitters on the anatomical target are already calibrated relative to the anatomy.

At step 280, the computer superimposes a representation of the location calculated in step 270 of the surgical device on the 3D anatomical image of the patient taken in step 220. The superimposed image is displayed to the user.

At step 290, the computer sends the appropriate signals to the motors to drive the surgical robot. If the user preprogrammed a trajectory, then the robot is driven so that the surgical instrument follows the preprogrammed trajectory if there is no further input from the user. If there is user input, then the computer drives the robot in response to the user input.

At step 295, the computer determines whether the procedure has been completed. If the procedure has not been completed, then the process beginning at step 250 is repeated.

At any time during the procedure, certain fault conditions may cause the computer to interrupt the program and respond accordingly. For instance, if the signal from the RF transmitters cannot be read, then the computer may be programmed to stop the movement of the robot or remove the surgical instrument from the patient. Another example of a fault condition is if the robot encounters a resistance above a preprogrammed tolerance level. Another example of a fault condition is if the RF transmitters on the anatomical target shift so that actual and calculated positions of the anatomy no longer match. One indicator that the anatomical target location has shifted relative to the transmitters is if the computer calculates that the surgical instrument appears to be inside bone when no drilling or penetration is actually occurring.

The proper response to each condition may be programmed into the system, or a specific response may be user-initiated. For example, the computer may determine that in response to an anatomy shift, the anatomy would have to be recalibrated, and the process beginning at step 230 should be repeated. Alternatively, a fault condition may require the flowchart to repeat from step 210. Another alternative is the user may decide that recalibration from step 230 is desired, and initiate that step himself.

Figure 12:
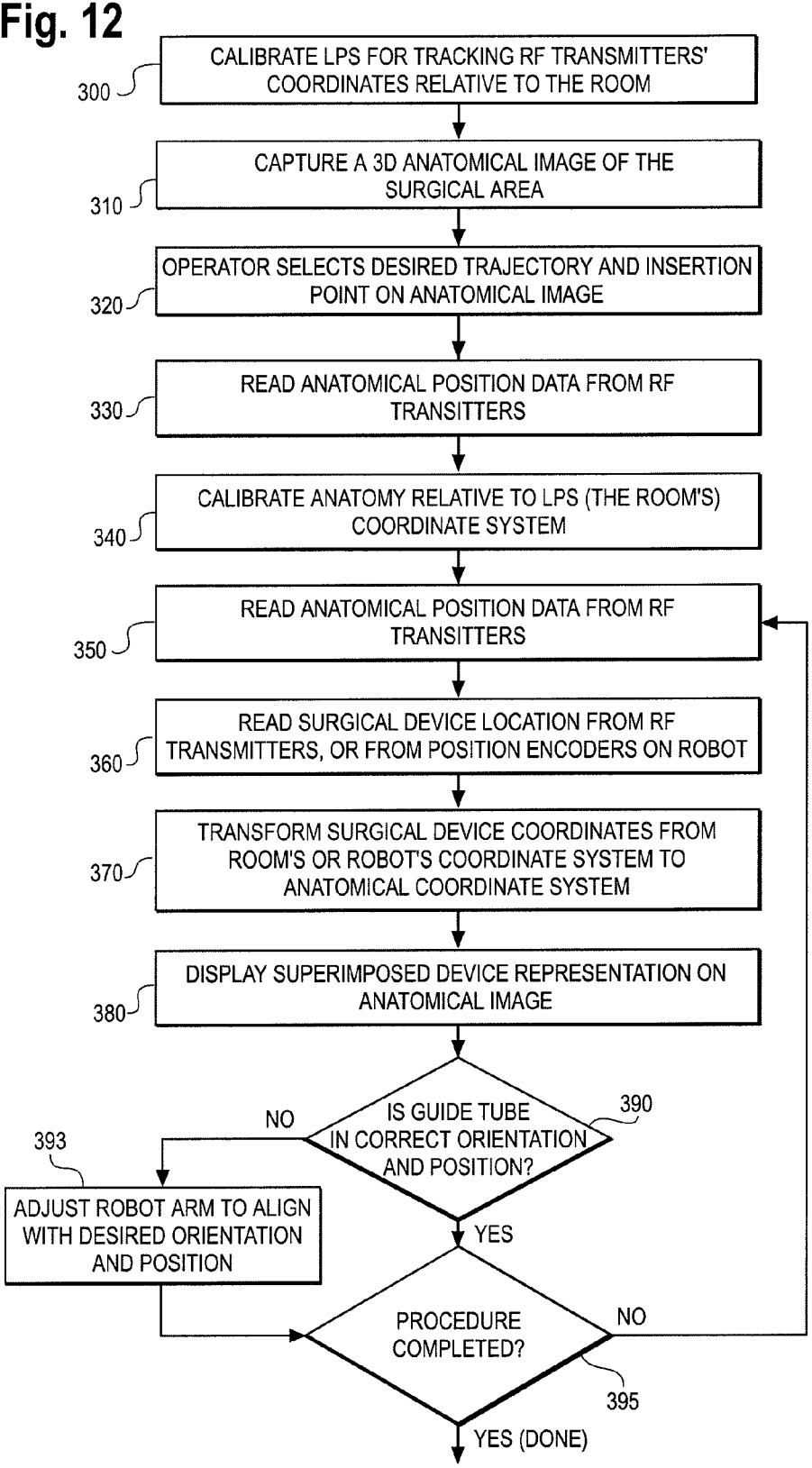
FIG. 12 is a flow chart diagram for a closed screw/needle insertion according to an embodiment of the present invention.

Referring now to FIG. 12, a flow chart diagram for a closed screw/needle insertion procedure according to an embodiment of the invention is shown. For example, in a closed pedicle screw insertion procedure, the robot holds a guide tube adjacent to the patient in the correct angular orientation and at the point where a pedicle screw is to be inserted through the tissue and into the bone of the patient.

The distance between each of the calibrating transmitters relative to each other is measured prior to calibration step 300. Each calibrating transmitter transmits RF signals on a different frequency so the positioning sensors can determine which transmitter emitted a particular RF signal. The signal of each of these transmitters is received by positioning sensors. Since the distance between each of the calibrating transmitters is known, and the sensors can identify the signals from each of the calibrating transmitters based on the known frequency, the positioning sensors are able to calculate, using time of flight calculation, the spatial distance of each of the positioning sensors relative to each other. The system is now calibrated. As a result, the positioning sensors can now determine the spatial position of any new RF transmitter introduced into the room relative to the positioning sensors.

At step 310, a 3D anatomical image scan, such as a CT scan, is taken of the anatomical target. Any 3D anatomical image scan may be used with the surgical robot and is within the scope of the present invention.

At step 320, the operator selects a desired trajectory and insertion point of the surgical instrument on the anatomical image captured at step 310. This desired trajectory and insertion point are programmed into the computer so that the robot can drive a guide tube automatically to follow the trajectory.

At step 330, the positions of the RF transmitters tracking the anatomical target are read by positioning sensors. These transmitters identify the initial position of the anatomical target and any changes in position during the procedure.

If any RF transmitters must transmit through a medium that changes the RF signal characteristics, then the system will compensate for these changes when determining the transmitter's position.

At step 340, the positions of the transmitters on the anatomy are calibrated relative to the LPS coordinate system. In other words, the LPS provides a reference system, and the location of the anatomical target is calculated relative to the LPS coordinates. To calibrate the anatomy relative to the LPS, the positions of transmitters affixed to the anatomical target are recorded at the same time as positions of temporary transmitters on precisely known landmarks on the anatomy that can also be identified on the anatomical image. This calculation is performed by a computer.

At step 350, the positions of the RF transmitters that track the anatomical target are read. Since the locations of the transmitters on the anatomical target have already been calibrated, the system can easily determine if there has been any change in position of the anatomical target.

At step 360, the positions of the transmitters on the surgical instrument are read. The transmitters may be located on the surgical instrument itself, and/or there may be transmitters attached to various points of the surgical robot.

In an embodiment of the invention, the surgical robot also includes a plurality of position encoders attached thereto that help determine the position of the surgical instrument. Position encoders are devices used to generate an electronic signal that indicates a position or movement relative to a reference position. There are many ways to generate a position signal, including for example, magnetic sensors, capacitive sensors, and optical sensors.

Position data read from the position encoders may be used to determine the position of the surgical instrument used in the procedure, and may be redundant of position data calculated from RF transmitters located on the surgical instrument. Therefore, position data from the position encoders may be used to double-check the position being read from the LPS.

At step 370, the coordinates of the positions of the transmitters on the surgical instrument, and/or the positions read from the position encoders, is transformed relative to the anatomical coordinate system. In other words, the position data of the surgical instrument is synchronized into the same coordinate system as the anatomy. This calculation is performed automatically by the computer since the positions of the transmitters on the anatomical target and the positions of the transmitters on the surgical instrument are in the same coordinate system and the positions of the transmitters on the anatomical target are already calibrated relative to the anatomy.

At step 380, the computer superimposes a representation of the location calculated in step 370 of the surgical device on the 3D anatomical image of the patient taken in step 310. The superimposed image is displayed to the user.

At step 390, the computer determines whether the guide tube is in the correct orientation and position to follow the trajectory planned at step 320. If it is not, then step 393 is reached. If it is in the correct orientation and position to follow the trajectory, then step 395 is reached.

At step 393, the computer determines what adjustments it needs to make in order to make the guide tube follow the preplanned trajectory. The computer sends the appropriate signals to drive the motors in order to correct the movement of the guide tube.

At step 395, the computer determines whether the procedure has been completed. If the procedure has not been completed, then the process beginning at step 350 is repeated.

At any time during the procedure, certain fault conditions may cause the computer to interrupt the program and respond accordingly. For instance, if the signal from the RF transmitters cannot be read, then the computer may be programmed to stop the movement of the robot or lift the guide tube away from the patient. Another example of a fault condition is if the robot encounters a resistance above a preprogrammed tolerance level. Another example of a fault condition is if the RF transmitters on the anatomical target shift so that actual and calculated positions of the anatomy no longer match. One indicator that the anatomical target location has shifted relative to the transmitters is if the computer calculates that the surgical instrument appears to be inside bone when no drilling or penetration is actually occurring.

The proper response to each condition may be programmed into the system, or a specific response may be user-initiated. For example, the computer may determine that in response to an anatomy shift, the anatomy would have to be recalibrated, and the process beginning at step 330 should be repeated. Alternatively, a fault condition may require the flowchart to repeat from step 300. Another alternative is the user may decide that recalibration from step 330 is desired, and initiate that step himself.

Figure 13:
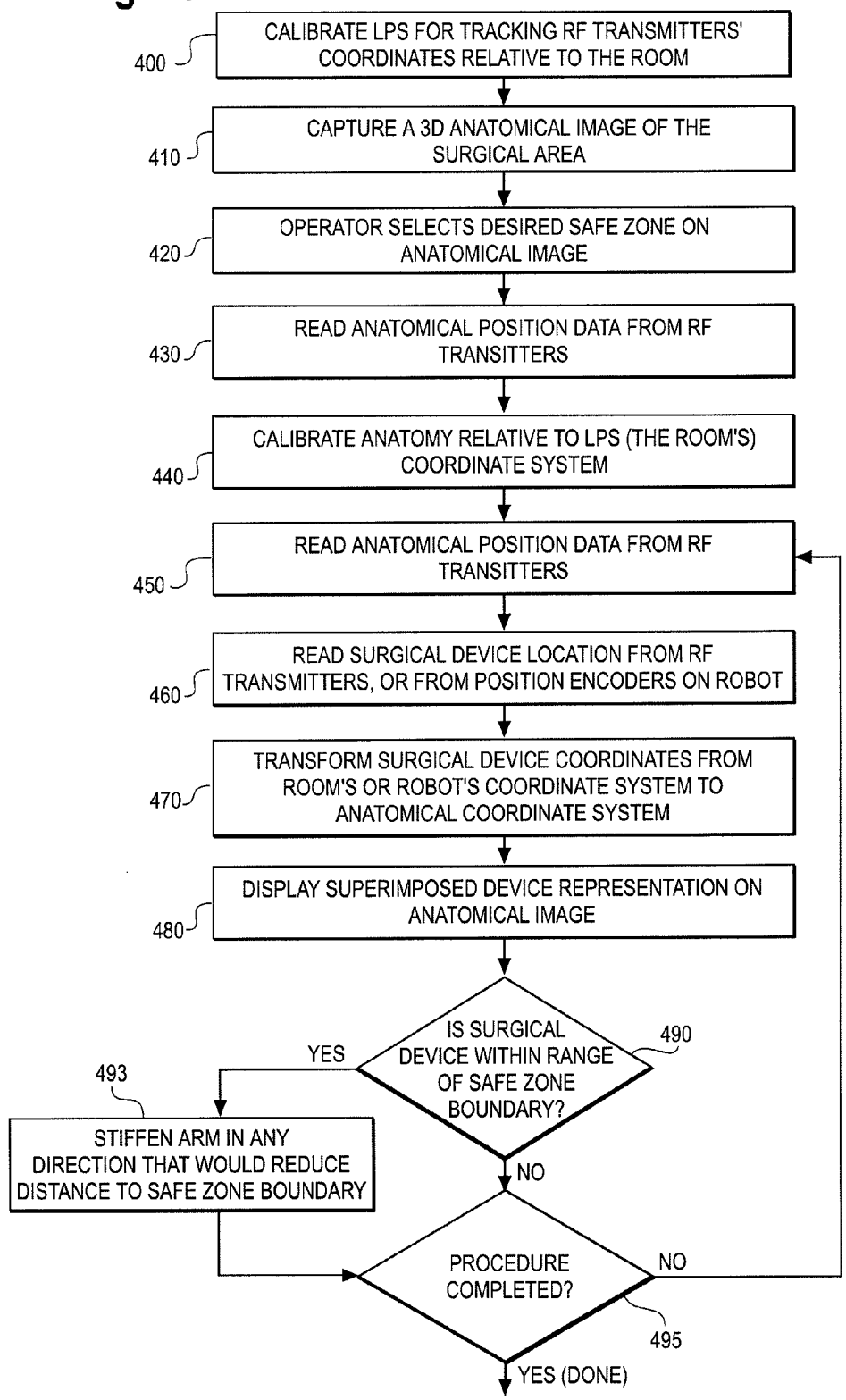
FIG. 13 is a flow chart diagram of a safe zone surgery according to an embodiment of the present invention.

Referring now to FIG. 13, a flow chart diagram for a safe zone surgical procedure according to an embodiment of the invention is shown. In a safe zone surgical procedure, there is a defined "safe zone" around the surgical area within which the surgical device must stay. The physician manually controls the surgical device that is attached to the end effectuator of the surgical robot. If the physician moves the surgical device to approach the boundary of the safe zone, then the surgical robot stiffens the arm so that the physician cannot move the instrument in any direction that would move the surgical device outside the safe zone.

The distance between each of the calibrating transmitters relative to each other is measured prior to calibration step 400. Each calibrating transmitter transmits RF signals on a different frequency so the positioning sensors can determine which transmitter emitted a particular RF signal. The signal of each of these transmitters is received by positioning sensors. Since the distance between each of the calibrating transmitters is known, and the sensors can identify the signals from each of the calibrating transmitters based on the known frequency, the positioning sensors are able to calculate, using time of flight calculation, the spatial distance of each of the positioning sensors relative to each other. The system is now calibrated. As a result, the positioning sensors can now determine the spatial position of any new RF transmitter introduced into the room relative to the positioning sensors.

At step 410, a 3D anatomical image scan, such as a CT scan, is taken of the anatomical target. Any 3D anatomical image scan may be used with the surgical robot and is within the scope of the present invention.

At step 420, the operator inputs a desired safe zone on the anatomical image taken in step 410. In an embodiment of the invention, the operator uses an input to the computer to draw a safe zone on a CT scan taken of the patient in step 410.

At step 430, the positions of the RF transmitters tracking the anatomical target are read by positioning sensors. These transmitters identify the initial position of the anatomical target and any changes in position during the procedure.

If any RF transmitters must transmit through a medium that changes the RF signal characteristics, then the system will compensate for these changes when determining the transmitter's position.

At step 440, the positions of the transmitters on the anatomy are calibrated relative to the LPS coordinate system.

In other words, the LPS provides a reference system, and the location of the anatomical target is calculated relative to the LPS coordinates. To calibrate the anatomy relative to the LPS, the positions of transmitters affixed to the anatomical target are recorded at the same time as positions of temporary transmitters on precisely known landmarks on the anatomy that can also be identified on the anatomical image. This calculation is performed by a computer.

At step 450, the positions of the RF transmitters that track the anatomical target are read. Since the locations of the transmitters on the anatomical target have already been calibrated, the system can easily determine if there has been any change in position of the anatomical target.

At step 460, the positions of the transmitters on the surgical instrument are read. The transmitters may be located on the surgical instrument itself, and/or there may be transmitters attached to various points of the surgical robot.

In an embodiment of the invention, the surgical robot also includes a plurality of position encoders attached thereto that help determine the position of the surgical instrument. Position encoders are devices used to generate an electronic signal that indicates a position or movement relative to a reference position. There are many ways to generate a position signal, including for example, magnetic sensors, capacitive sensors, and optical sensors.

Position data read from the position encoders may be used to determine the position of the surgical instrument used in the procedure, and may be redundant of position data calculated from RF transmitters located on the surgical instrument. Therefore, position data from the position encoders may be used to double-check the position being read from the LPS.

At step 470, the coordinates of the positions of the transmitters on the surgical instrument, and/or the positions read from the position encoders, is transformed relative to the anatomical coordinate system. In other words, the position data of the surgical instrument is synchronized into the same coordinate system as the anatomy. This calculation is performed automatically by the computer since the positions of the transmitters on the anatomical target and the positions of the transmitters on the surgical instrument are in the same coordinate system and the positions of the transmitters on the anatomical target are already calibrated relative to the anatomy.

At step 480, the computer superimposes a representation of the location calculated in step 470 of the surgical device on the 3D anatomical image of the patient taken in step 410. The superimposed image is displayed to the user.

At step 490, the computer determines whether the surgical device attached to the end effectuator of the surgical robot is within a specified range of the safe zone boundary, for example, within 1 millimeter of reaching the safe zone boundary. If the end effectuator is almost to the boundary, then step 493 is reached. If it is well within the safe zone boundary, then step 495 is reached.

At step 493, the computer stiffens the arm of the surgical robot in any direction that would allow the user to move the surgical device closer to the safe zone boundary.

At step 495, the computer determines whether the procedure has been completed. If the procedure has not been completed, then the process beginning at step 450 is repeated.

At any time during the procedure, certain fault conditions may cause the computer to interrupt the program and respond accordingly. For instance, if the signal from the RF transmitters cannot be read, then the computer may be programmed to stop the movement of the robot or remove the surgical instrument from the patient. Another example of a fault condition is if the robot encounters a resistance above a preprogrammed tolerance level. Another example of a fault condition is if the RF transmitters on the anatomical target shift so that actual and calculated positions of the anatomy no longer match. One indicator that the anatomical target location has shifted relative to the transmitters is if the computer calculates that the surgical instrument appears to be inside bone when no drilling or penetration is actually occurring.

The proper response to each condition may be programmed into the system, or a specific response may be user-initiated. For example, the computer may determine that in response to an anatomy shift, the anatomy would have to be recalibrated, and the process beginning at step 430 should be repeated. Alternatively, a fault condition may require the flowchart to repeat from step 400. Another alternative is the user may decide that recalibration from step 430 is desired, and initiate that step himself.

Figure 14:
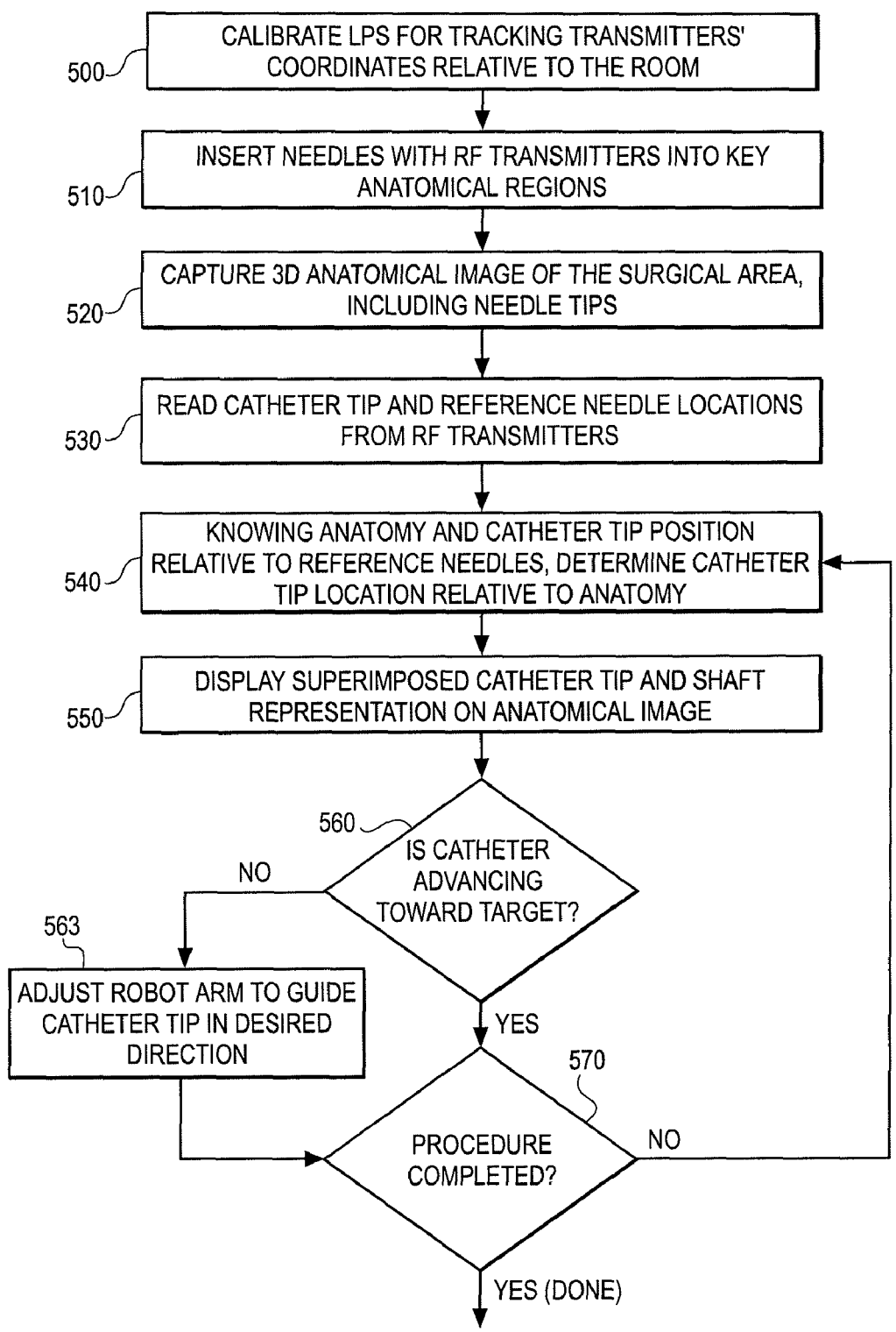
FIG. 14 is a flow chart diagram of a flexible catheter insertion procedure according to an embodiment of the present invention.

Referring now to FIG. 14, a flow chart diagram for a flexible catheter or wire insertion procedure via a straight or curved path according to an embodiment of the invention is shown. Catheters are used in a variety of medical procedures to deliver medicaments to a specific site in a patient's body. Often, delivery to a specific location is needed so a targeted diseased area can then be treated. Sometimes instead of inserting the catheter directly, a flexible wire is first inserted, over which the flexible catheter can be slid.

The distance between each of the calibrating transmitters relative to each other is measured prior to calibration step 500. Each calibrating transmitter transmits RF signals on a different frequency so the positioning sensors can determine which transmitter emitted a particular RF signal. The signal of each of these transmitters is received by positioning sensors. Since the distance between each of the calibrating transmitters is known, and the sensors can identify the signals from each of the calibrating transmitters based on the known frequency, the positioning sensors are able to calculate, using time of flight calculation, the spatial distance of each of the positioning sensors relative to each other. The system is now calibrated. As a result, the positioning sensors can now determine the spatial position of any new RF transmitter introduced into the room relative to the positioning sensors.

At step 510, reference needles that contain the RF transmitters are inserted into the body. The purpose of these needles is to track movement of key regions of soft tissue that will deform during the procedure or with movement of the patient.

At Step 520, a 3D anatomical image scan, such as a CT scan, is taken of the anatomical target. Any 3D anatomical image scan may be used with the surgical robot and is within the scope of the present invention. The anatomical image capture area includes the tips of the reference needles so that their transmitters' positions can be determined relative to the anatomy At step 530, the RF signals from the catheter tip and reference needles are read.

At step 540, the position of the catheter tip is calculated. Because the position of the catheter tip relative to the reference needles and the positions of the reference needles relative to the anatomy are known, the computer can calculate the position of the catheter tip relative to the anatomy.

At step 550, the superimposed catheter tip and the shaft representation is displayed on the anatomical image taken in step 520.

At step 560, the computer determines whether the catheter tip is advancing toward the anatomical target along the pre-chosen path (straight or curved). If it is not moving along the correct path to the anatomical target, then step 563 is reached. If it is correctly moving, then step 570 is reached.

At step 563, the robot arm is adjusted to guide the catheter tip in the desired direction. If the anatomy needs to be calibrated, then the process beginning at step 520 is repeated. If the anatomy does not need to be recalibrated, then the process beginning at step 540 is repeated.

At step 570, the computer determines whether the procedure has been completed. If the procedure has not been completed, then the process beginning at step 540 is repeated.

At any time during the procedure, certain fault conditions may cause the computer to interrupt the program and respond accordingly. For instance, if the signal from the RF transmitters cannot be read, then the computer may be programmed to stop the movement of the robot or remove the flexible catheter from the patient. Another example of a fault condition is if the robot encounters a resistance above a preprogrammed tolerance level. Another example of a fault condition is if the RF transmitters on the anatomical target indicate that the location of the anatomical target shift so that actual and calculated positions of the anatomy no longer match. One indicator that the anatomical target location has shifted relative to the transmitters is if the computer calculates that the surgical instrument appears to be inside bone when no drilling or penetration is actually occurring.

The proper response to each condition may be programmed into the system, or a specific response may be user-initiated. For example, the computer may determine that in response to an anatomy shift, the anatomy would have to be recalibrated, and the process beginning at step 520 should be repeated. Alternatively, a fault condition may require the flowchart to repeat from step 500. Another alternative is the user may decide that recalibration from step 520 is desired, and initiate that step himself.

Figure 15A:
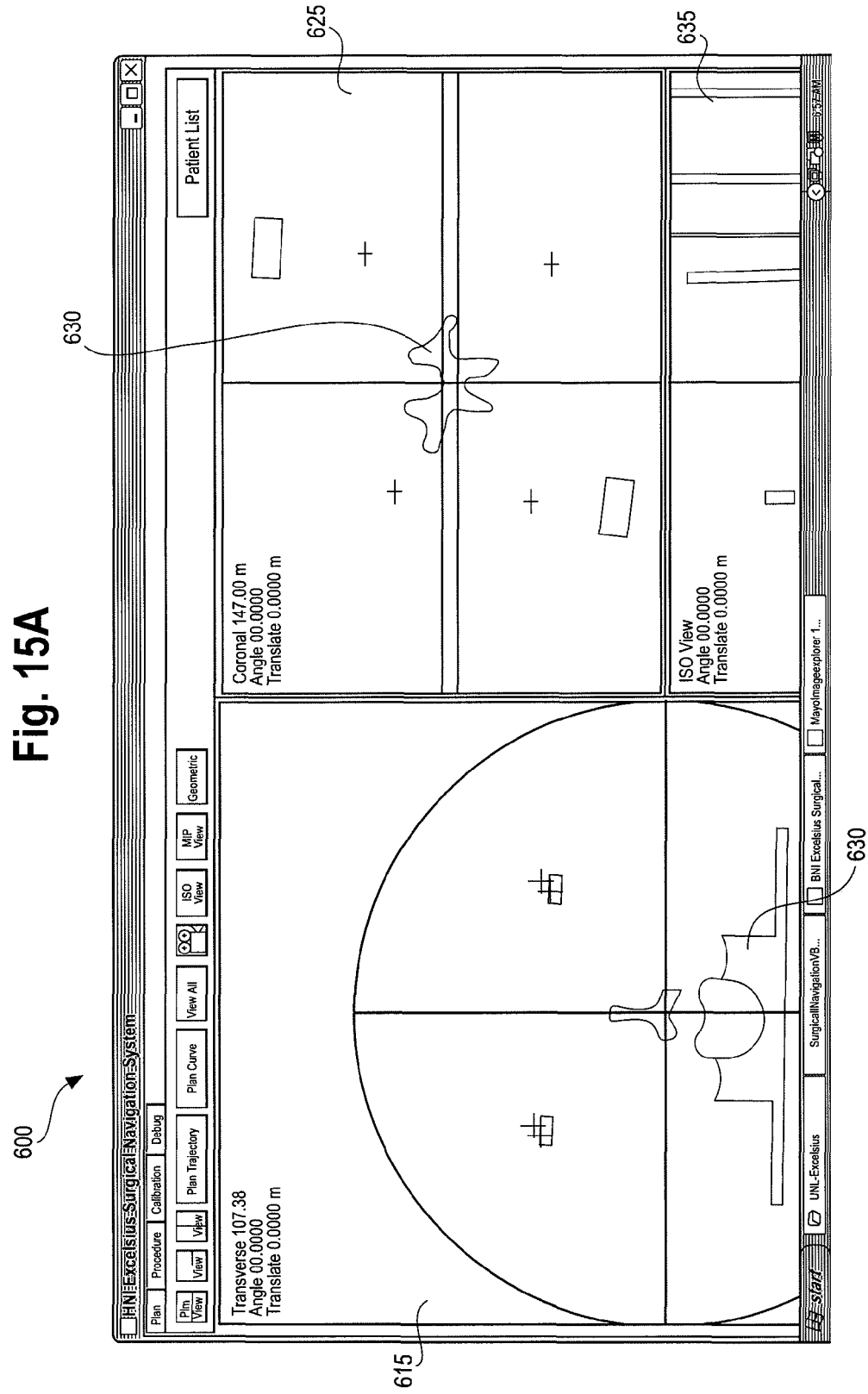
FIG. 15A shows a screenshot of a monitor display showing a set up of the anatomy in X, Y and Z views according to an embodiment of the present invention.
Figure 15B:
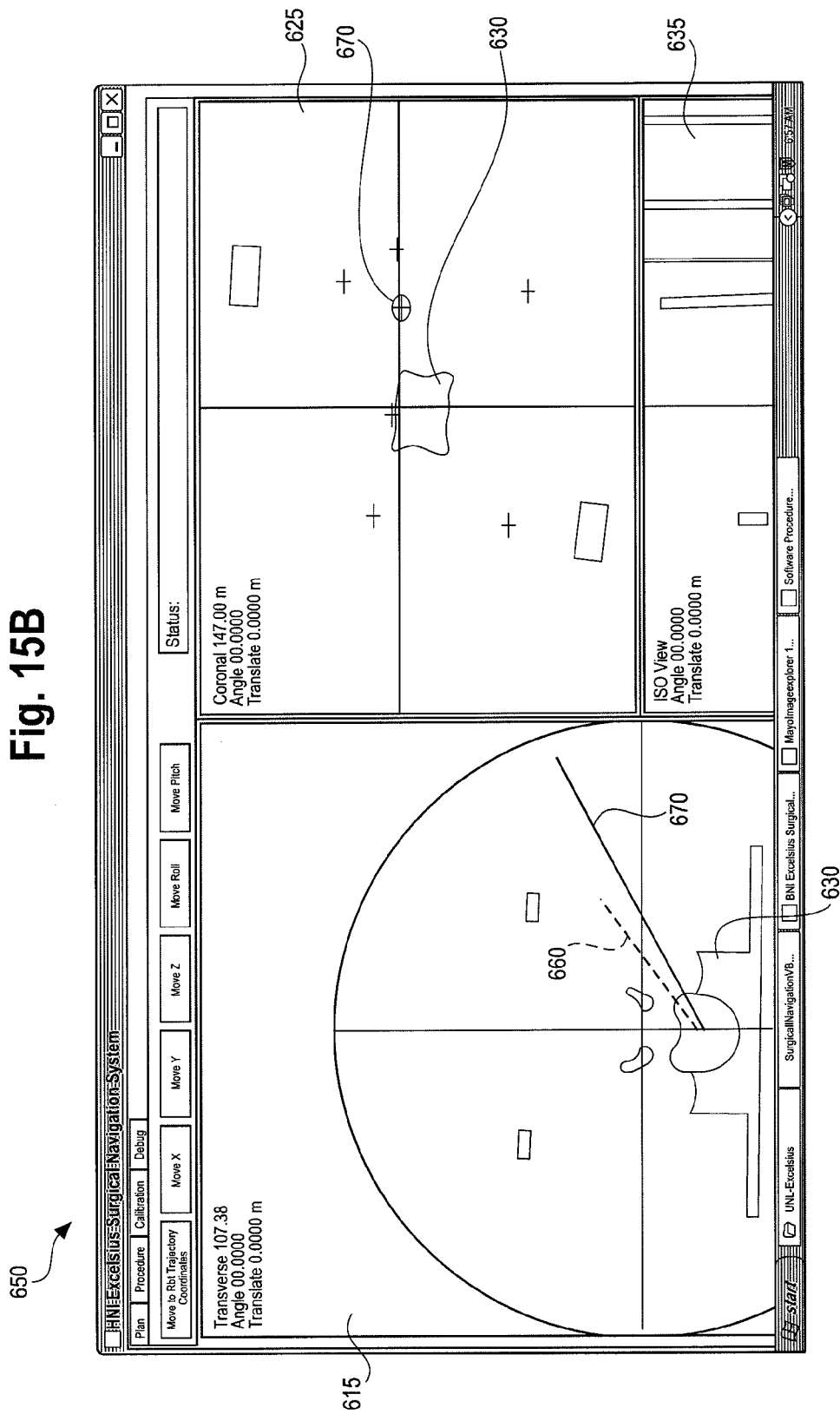
FIG. 15B shows a screenshot of a monitor display showing what the user views during an invasive procedure according to an embodiment of the present invention.

Referring now to FIGS. 15A & 15B, screenshots of software for use with an embodiment of the invention are provided. The software provides the method to select the target area of surgery, plan the surgical path, check the planned trajectory of the surgical path, synchronize the medical images to the positioning system and precisely control the positioning system during surgery. The surgical positioning system and navigation software includes an optical guidance system or RF Local Positioning System (RF-LPS), which are in communication with the positioning system.

FIG. 15A shows a screen shot 600 of the selection step for a user using the software program. Screen shot 600 includes windows 615, 625, and 635, which show a 3D anatomical image of surgical target 630 on different planes. In this step, the user selects the appropriate 3D image corresponding to anatomical location of where the procedure will occur. The user uses a graphic control to change the perspective of the image in order to more easily view the image from different angles. The user can view the surgical target 630 separate coordinate views for each of the X, Y and Z axis for each anatomical location in the database in each window 615, 625 and 635, respectively.

After selecting the desired 3D image of the surgical target 630, the user will plan the appropriate trajectory on the selected image. An input control is used with the software in order to plan the trajectory of the surgical instrument. In one embodiment of the invention, the input control is in the shape of a biopsy needle for which the user can plan a trajectory.

FIG. 15B shows a screen shot 650 during the medical procedure. The user can still view the anatomical target 630 in different x, y and z coordinate views on windows 615, 625, and 635.

In screen shot 650, the user can see the planned trajectory line 670 in multiple windows 615, 625, and 635 if the planned trajectory line falls within these regions. The actual trajectory and location of the surgical instrument 660 is superimposed on the image. The actual trajectory and location of the surgical instrument 660 is dynamically updated and displayed.

Figure 16:
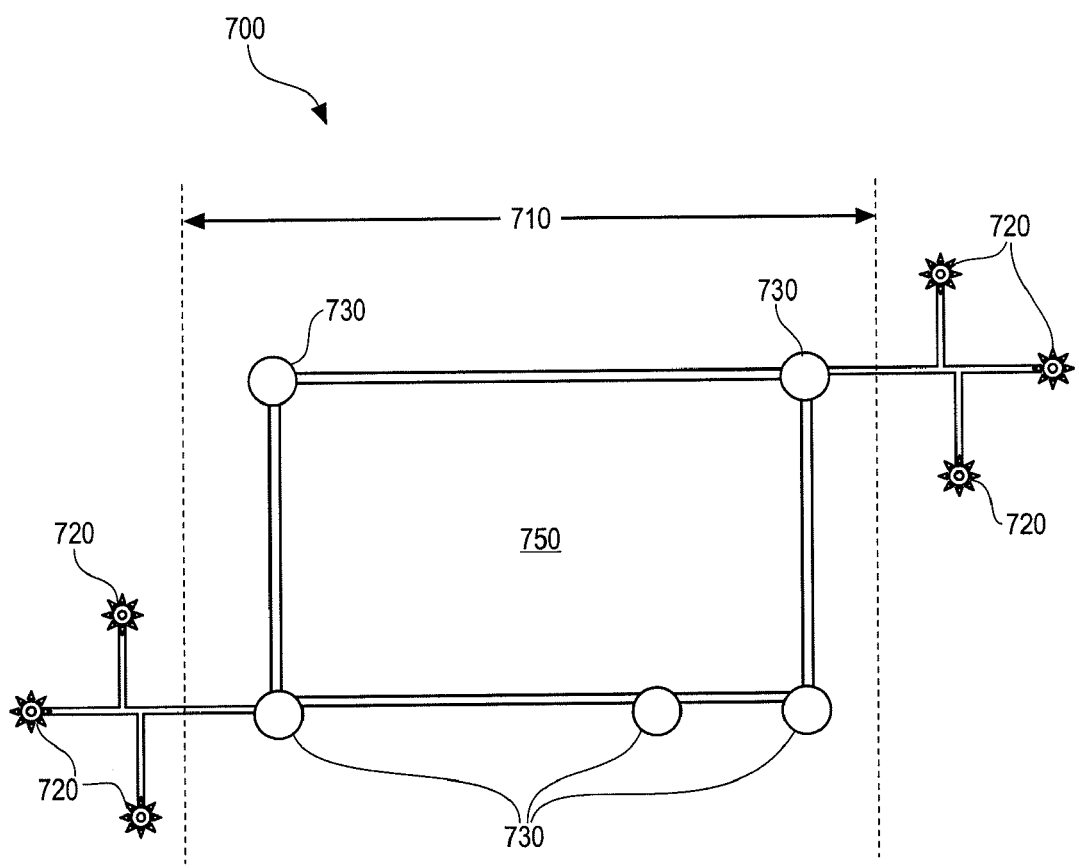
FIG. 16 shows the use of a calibration frame with the guidance system according to an embodiment of the present invention.

As described earlier, the surgical robot can be used with alternate guidance systems other than an LPS. One embodiment of the invention contemplates the use of a calibration frame for use with the guidance system, as shown in FIG. 16. A calibration frame 700 can be used in connection with many invasive procedures; for example, it can be used in thoracolumbar pedicle screw insertion in order to help achieve a more accurate trajectory position.

The use of the calibration frame 700 simplifies the calibration procedure. The calibration frame 700 comprises a combination of radio-opaque markers 730 and infrared, or "active", markers 720. The radio-opaque markers 730 are located within the CT scan region 710, and the active markers are located outside of the CT scan region 710. A surgical field 750, the area where the invasive procedure will occur, is located within the perimeter created by radio-opaque markers 730. The actual distances of the radio-opaque and active markers relative to each other is measured from a high-precision laser scan of the calibration frame. Further, active markers are also placed on the robot (not shown).

The calibration frame 700 is mounted on the patient's skin before surgery/biopsy, and will stay mounted during the entire procedure. Surgery/biopsy takes place through the center of the frame.

When the region of the plate with the radio-opaque markers 730 is scanned intraoperatively or prior to surgery in, for example, a computed tomography (CT) scanner, the CT scan contains both the medical images of the patient's bony anatomy and spherical representations of the radio-opaque markers 730. Software is used to determine the locations of the centers of the spheres relative to the trajectories defined by the surgeon on the medical images.

Because the system knows the positions of the trajectories relative to the radio-opaque markers 730, the positions of the radio-opaque markers 730 relative to the active markers 720, and the positions of the active markers 720 on the calibration frame 700 relative to the active markers on the robot (not shown), the system has all information necessary to position the robot's end effectuator relative to the defined trajectories.

One aspect of the software disclosed herein is a unique algorithm for locating the center of the above-described spheres that takes advantage of the fact that a CT scan consists of slices typically spaced 1.5 mm or more apart in the z direction but sampled with about 0.3 mm resolution in the x and y directions. Since the diameter of the radio-opaque spheres is several times larger than this slice spacing, different z slices of the sphere will appear as circles of different diameters on each successive xy planar slice. Since the diameter of the sphere is defined beforehand, the necessary z position of the center of the sphere relative to the slices can be calculated that achieves the given set of circles of various diameters. This algorithm provides, for example, the center of a large sphere more precisely than other methods could find the center of a sphere that is closer in diameter to the slice thickness.

To provide further illustration of how the calibration plate works according to an embodiment of the invention, the steps of a closed screw/needle insertion procedure utilizing a calibration frame is described. First, a calibration frame 700 is attached to the patient's skin in the region at which surgery/biopsy is to take place. Next, the patient receives a CT scan either supine or prone, whichever positioning orients the calibration frame upward. Thereafter, the surgeon manipulates three planar views of the patient's CT images with rotations and translations. The surgeon then draws trajectories on the images that define the desired position and strike angle of the end effectuator.

The robot then will move to the desired position. If forceful resistance beyond a pre-set tolerance is exceeded, the robot will halt. The robot holds the guide tube at the desired position and strike angle to allow the surgeon to insert a screw or needle. If tissues move in response to applied force or due to breathing, the movement will be tracked by optical markers and the robot's position will automatically be adjusted.

As a further illustration of a procedure using an alternate guidance system, the steps of an open screw insertion procedure utilizing an optical guidance system is described. After surgical exposure, a small tree of optical markers is attached to a bony prominence in the area of interest. Calibration procedures standard for image guidance are used to establish the anatomy relative to the optical tracking system and medical images.

The surgeon manipulates three planar views of the patient's CT images with rotations and translations. The surgeon then draws trajectories on the images that define the desired position and strike angle of the end effectuator.

The robot moves to the desired position. If forceful resistance beyond a pre-set tolerance is exceeded, the robot will halt. The robot holds the guide tube at the desired position and strike angle to allow the surgeon to insert a screw. If tissues move in response to applied force or due to breathing, the movement will be tracked by optical markers and the robot's position will automatically be adjusted.

From the foregoing it will be observed that numerous modifications and variations can be effectuated without departing form the true spirit and scope of the novel concepts of the present invention. It is to be understood that no limitation with respect to the specific embodiments illustrated is intended or should be inferred. The disclosure is intended to cover by the appended claims all such modifications as fall within the scope of the claims.

What is claimed is:

1. A system performing an invasive medical procedure using an instrument, comprising:
    a robot having an effectuator element, the effectuator element forming or being configured to securely hold the instrument that is adapted to be positioned at a desired position within or outside a patient's body;
    two or more RF effectuator transmitters affixed to the effectuator element at desired locations thereof;
    a plurality of RF receivers that receive a signal from the two or more RF effectuator transmitters;
    an effectuator active marker affixed to the effectuator element;
    a calibration frame adapted to be mounted to the patient's skin, the calibration frame comprising a plurality of frame markers, the plurality of frame markers comprising at least one radio opaque frame marker located within a computed tomography scan region of the desired position and at least one active frame marker located outside the computed tomography scan region of the desired position;
    a motor assembly that is mounted on the robot, and that is adapted to move the effectuator element in each one of the x, y and z directions independently of movement in the others of the x, y and z directions, the x, y and z directions being perpendicular to each other; and
    a control unit operatively coupled to the motor assembly, the control unit receives a desired point of insertion into the patient and trajectory of the instrument to an anatomical target within the patient, a position of at least one radio opaque frame marker relative to the desired trajectory, a position of the at least one radio opaque frame marker relative to the at least one active frame marker, a position of the at least one active frame marker relative to the effectuator active marker, the control unit supplying signals to the motor assembly to cause the motor assembly to selectively move the effectuator element along the x, y and z directions, the control unit configured (i) to calculate the position of the two or more RF effectuator transmitters relative to the anatomical target by analysis of radio frequency signals emitted by the two or more RF effectuator transmitters based upon the received relative positions of the respective radio opaque and active frame markers, (ii) to show an actual position and actual trajectory of the instrument and the desired trajectory superimposed over an anatomical image of the patient's body shown on a display, (iii) to control actuation of the motor assembly to move along the desired trajectory from the desired point of insertion to the desired position within or outside a patient's body based on the radio frequency signals and received relative positions of the radio opaque and active frame markers, and (iv) to selectively energize the two or more RF effectuator transmitters to ablate tissue and cause at least a portion of the effectuator element to move in the desired trajectory.

2. The system of claim 1, wherein the effectuator element comprises a tube having a pitch axis, a roll axis and a tube axis defining an axis of rotation of the tube.

3. The system of claim 1, wherein the effectuator element comprises a needle.

4. The system of claim 1, wherein the effectuator element includes a beveled leading edge, wherein at least one of the RF transmitters of the two or more RF transmitters affixed to the effectuator element is positioned on a distal end of the effectuator element, RF energy emitted therefrom produces a force that balances the mechanical displacement force created by the beveled edge of the effectuator element.

5. The system of claim 1, wherein the effectuator element includes a non-beveled leading edge that can ablate a pathway through tissue to reach the target position.

6. The system of claim 1, wherein the plurality of RF receivers comprises three or more RF receivers.

7. The system of claim 1, wherein the control unit is configured to receive information from the plurality of RF receivers in an iterative fashion.

8. The system of claim 1, wherein the control unit is configured to receive information from the plurality of RF receivers in a dynamic fashion.

9. The system of claim 1, wherein the control unit is configured to allow a user to pick a desired location within a human body and to dynamically provide information that allows the motor assembly to move the effectuator element to the desired location.

10. The system of claim 1, wherein the control unit comprises a computer.

11. The system of claim 1, wherein a leading edge of the effectuator element is configured to have an RF transmitter affixed thereto.

12. The system of claim 1, wherein the control unit is configured to cause the RF transmitter to emit RF signals at desired times.

13. The system of claim 12, wherein the control unit is configured to cause the RF transmitter to emit RF signals at desired frequencies.

14. The system of claim 1, wherein the two or more RF transmitters attached to the effectuator element are configured to generate an ablation field to cause at least a portion of the effectuator element to move by selectively reducing resistance to penetration in any direction.

15. The system of claim 1, wherein the two or more RF transmitters of the effectuator element comprises at least three RF transmitters affixed to the effector element at desired locations thereof, the controller configured to selectively energize the three RF transmitters being selectively energizable to ablate tissue and cause at least a portion of the effectuator element to move in the desired trajectory.

16. The system of claim 15, wherein the at least three RF transmitters attached to the effectuator element are configured to generate an ablation field to cause at least a portion of the effectuator element to move by selectively reducing resistance to penetration in any direction.

17. The system of claim 16, wherein the at least three RF transmitters attached to the effectuator element are adapted to have three RF transmitters evenly radially distributed around the effectuator element.

18. The system of claim 17, wherein the at least three RF transmitters attached to the effectuator element are affixed to a distal end of the effectuator element.

19. The system of claim 18, wherein at least one of the at least three RF transmitters attached to the effectuator element is located on a leading edge of the effectuator element.

* * * * *